United States Patent [19]
Kermode et al.

[11] Patent Number: 5,769,865
[45] Date of Patent: Jun. 23, 1998

[54] INSTRUMENT AND METHOD FOR TRANSECTION OF A LIGAMENT

[75] Inventors: Jim Kermode, Sunnyvale, Calif.; David Kermode, Pella, Iowa; Mark Clifford, Los Altos; Wade Keller, San Jose, both of Calif.

[73] Assignee: Surgical Insight, Inc., Sunnyvale, Calif.

[21] Appl. No.: 805,464

[22] Filed: Feb. 25, 1997

[51] Int. Cl.$^6$ ..................................................... A61B 17/32
[52] U.S. Cl. ........................... 606/167; 606/170; 606/192; 604/22; 604/96; 128/898
[58] Field of Search ..................................... 606/159, 167, 606/170, 185, 180, 192; 128/898; 604/22, 96

[56] References Cited

U.S. PATENT DOCUMENTS

| | | |
|---|---|---|
| 4,962,770 | 10/1990 | Agee et al. . |
| 4,979,951 | 12/1990 | Simpson . |
| 5,000,518 | 3/1991 | Yock . |
| 5,029,573 | 7/1991 | Chow . |
| 5,179,963 | 1/1993 | Berger . |
| 5,269,796 | 12/1993 | Miller et al. . |
| 5,273,024 | 12/1993 | Menon et al. . |
| 5,323,765 | 6/1994 | Brown . |
| 5,325,883 | 7/1994 | Orr . |
| 5,331,975 | 7/1994 | Bonutti . |
| 5,366,465 | 11/1994 | Mirza . |
| 5,423,804 | 6/1995 | Kulick . |
| 5,425,355 | 6/1995 | Kulick . |
| 5,458,611 | 10/1995 | Resnick et al. . |

FOREIGN PATENT DOCUMENTS

WO 96/20749  7/1996  WIPO .

OTHER PUBLICATIONS

M.A. Mirza et al., "Newer Techniques of Carpal Tunnel Release," *Orthopedic Clinics of North America* (Apr. 1996) 72(2): 355–371.

N. Einhorn et al., "Pitfalls of Endoscopic Carpal Tunnel Release," *Orthopedic Clinics of North America* (Apr. 1996) 27(2): 373–380.

E. Akelman et al., "Carpal Tunnel Syndrome," *Orthopedic Clinics of North America* (Oct. 1995) 26(4): 769–778.

M. Lewis, "Carpal Tunnel Syndrome Hits a Costly Nerve with Companies," *American Machinist* (Jan. 1997) pp. 49–51.

*Primary Examiner*—Michael Buiz
*Assistant Examiner*—David O. Reip
*Attorney, Agent, or Firm*—Towsend and Townsend and Crew LLP

[57] ABSTRACT

In a procedure for the treatment of carpal tunnel syndrome, the carpal ligament is spread by use of a cutting device passing through the interior of a cannula inserted into the carpal tunnel through an incision in the patient's wrist, the cannula containing an inflatable balloon at its distal end to secure the position of the cutting device against the carpal ligament, and the cutting device comprising a blade whose position is remotely controlled from the proximal end of the device. Other features of the procedure are the use of a blunt-tipped hypodermic needle and exchange wire to establish a path to the site under the carpal ligament, an endoscope or other visualization device to be inserted through the cannula with the cutting device, and a removable sheath over the cannula to contain the inflatable balloon until inflation is desired.

31 Claims, 7 Drawing Sheets

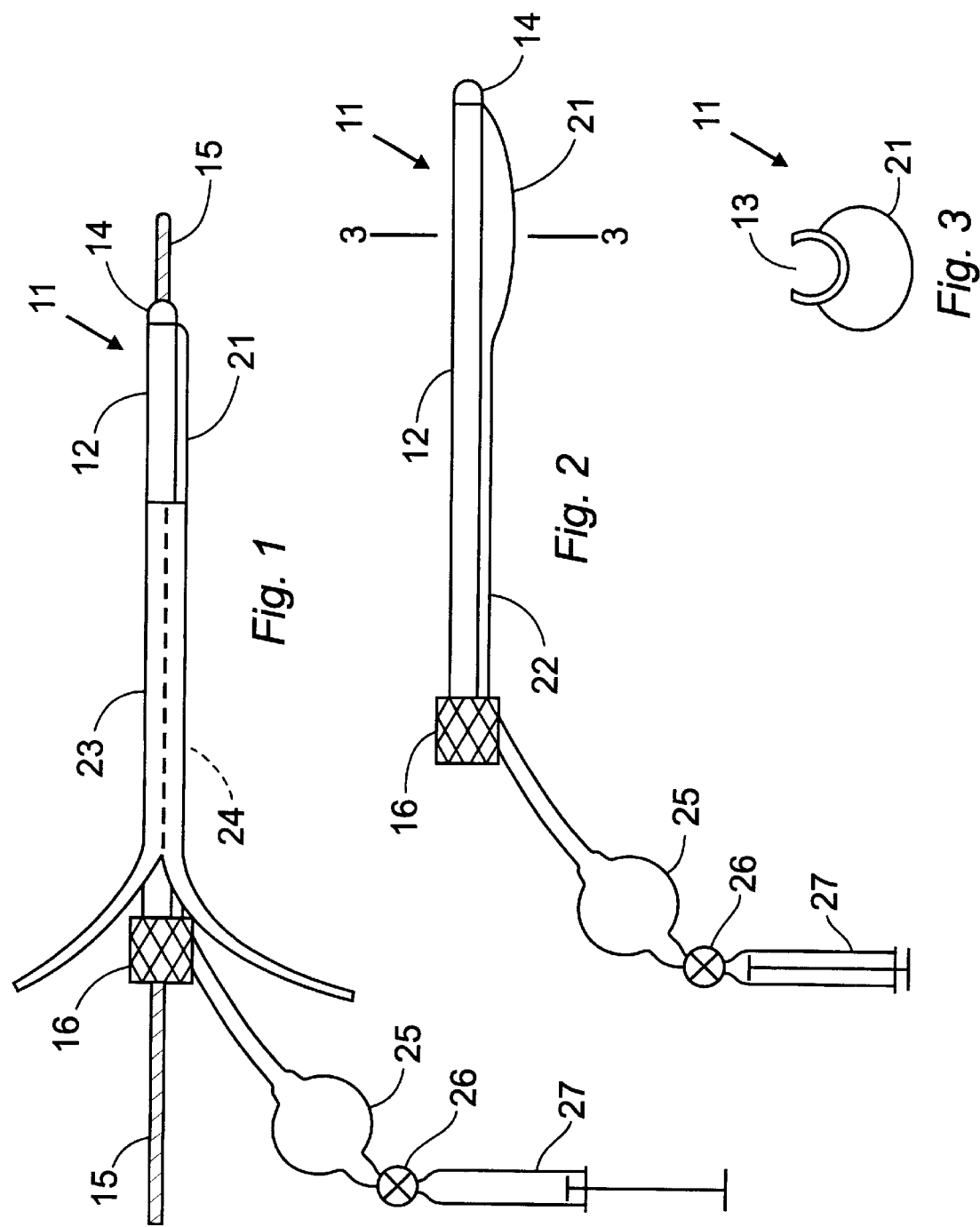

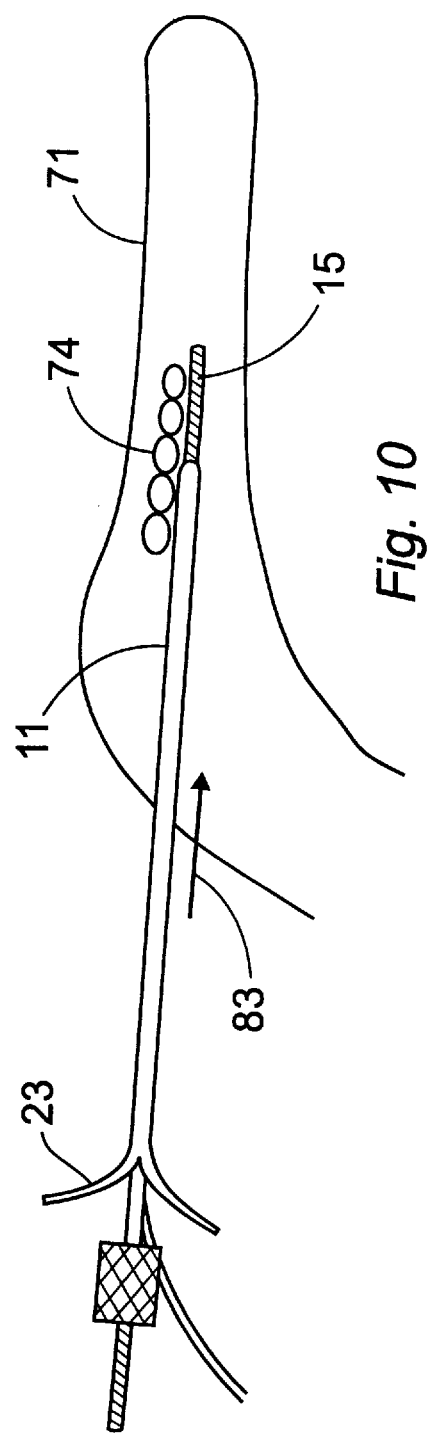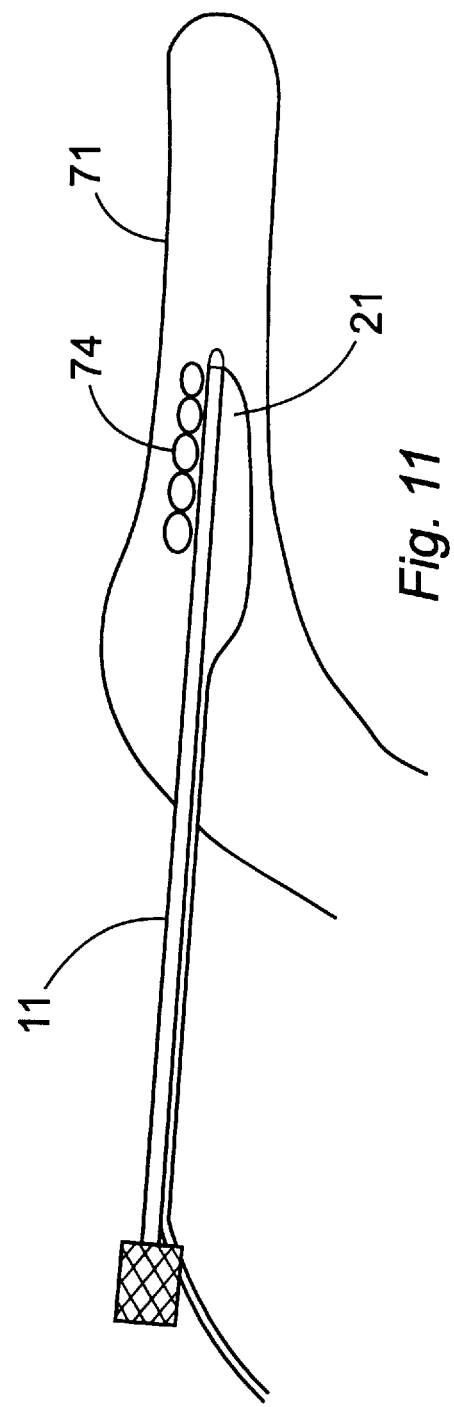

INSTRUMENT AND METHOD FOR TRANSECTION OF A LIGAMENT

This invention resides in the field of treatments for carpal tunnel syndrome and other physiological conditions treatable by transection of a ligament.

BACKGROUND OF THE INVENTION

Carpal tunnel syndrome is an extremely debilitating condition caused by compression of the median nerve within the carpal tunnel. The compression may stem from a variety of conditions, including repetitive movements of the hand or wrist, as well as rheumatoid arthritis, and edema in the final trimester of pregnancy. The compression interferes with the function of the median nerve, and its symptoms include numbness and tingling in the fingers and in some cases pain radiating as far as the shoulder or base of the neck. Ultimate effects may include an impaired grasping ability, loss of sleep from pain, numbness in the hand, and weakness or atrophy of the thenar muscles.

One method of treatment is the injection of cortisone or other medications into the carpal tunnel. If symptoms persist or recur, however, or if the patient experiences severe sensory deficit or loss of function in the thenar muscles, treatment is indicated which involves surgical division or release of the carpal ligament which forms the anterior (palm-side) wall of the carpal tunnel and extends in a direction transverse to the carpal tunnel.

Traditional methods of releasing the transverse carpal ligament involve open wrist surgery, in which the carpal ligament is divided by a deep longitudinal incision through the palm. The skin is then sutured and the procedure, which can be done on an outpatient basis, is completed in less than a half hour. The patient then wears a splint for approximately one to three weeks. Procedures of this type do not involve entry into the carpal tunnel, but they leave a noticeable scar on the patient's wrist and palm, and entail a long recovery time. Patients whose occupations do not require extensive use of the hands can generally return to work within a few days. In the majority of cases, however, the syndrome is occupationally related, and the persistent tenderness in the palm as the scar matures can leave the patient disabled for six weeks or more. Most patients experience tenderness in the heel of the hand for four to six months following the surgery.

The surgical alternative to open wrist surgery is endoscopic carpal tunnel release. One such procedure is described by Chow, J. C., in Chow, J. C., "Endoscopic release of the carpal ligament: A new technique for carpal tunnel syndrome," *Arthroscopy* 5:19–34 (1989); Chow, J. C., "The Chow technique of endoscopic release of the carpal ligament for carpal tunnel syndrome: four years of clinical results," *Arthroscopy* 9:301–314 Chow, J. C., U.S. Pat. No. 5,029,573, issued Jul. 9, 1991. According to this procedure, entry and exit incisions are made in the patient's wrist and palm, respectively. A slotted cannula is inserted beneath the carpal ligament into the carpal tunnel itself, between the two incisions, and an endoscope is placed in the cannula. Specialized scalpels protruding through the opening in the cannula are then used to divide the carpal ligament, the endoscope and scalpels capable of being inserted into the cannula from either end.

A second endoscopic procedure has been developed by Agee, J. M., and described in Agee, J. M., et al., "Endoscopic release of the carpal tunnel: A randomized prospective multicenter study," *J. Hand Surg. Am.* 17:97–95 (1992); and Agee, J. M., et al., U.S. Pat. No. 4,962,770, issued Oct. 16, 1990. The Agee system is similar to the Chow system except that only a single entry is made, the entry being on the patient's wrist. Here as well, a specialized scalpel and endoscope assembly are used to effect division of the carpal ligament.

Both the Chow and Agee systems involve fairly large cannulae, which are bulky and cumbersome to use. Since the cannulae are placed blindly, the procedures entail a risk of damage to nerves or arteries located near the carpal tunnel. Furthermore, the cutting blades in these systems are difficult to manipulate and require very careful control by the physician operator.

These and other shortcomings of the prior art are addressed by the present invention.

SUMMARY OF THE INVENTION

This invention resides in a composite device and method for partial or complete division of a ligament by endoscopic means. The device and method are useful for the treatment of carpal tunnel syndrome and other physiological conditions that are characterized by a constrained ligament or a ligament exerting unfavorably high pressure on an adjacent nerve or structure. Both the device and method of this invention present a variety of novel features. One such feature of the composite device is a cannula that serves to guide the operative components of the system through the carpal tunnel, to the site of interest on the posterior side of the ligament. In the case of ligaments in general, the cannula guides the operative components through a passage that is adjacent and transverse to the ligament. The term "adjacent" as used herein includes both above and below, although it will be clear to the experienced physician that one or the other will be preferable for any particular ligament. The term "transverse" as used herein means that the passage traverses the axis of the ligament. This includes traversing at right angles as well as at acute or obtuse angles. A lateral opening on one side of the cannula permits access of operative components inside the cannula to the surrounding tissue, or permits the entry of inflamed or bulky tissue into the cannula for severance and removal inside the cannula. An inflatable member or balloon on the opposite side of the cannula urges the lateral opening, and any operative components that are present in the cannula interior adjacent to the opening, against the ligament. Inflation and deflation of the balloon are controlled from the proximal end of the cannula. A further novel feature is the use of a wire (referred to herein as either a guidewire or an exchange wire) to direct the placement of the cannula prior to insertion of the operative component(s), and the insertion of the operative component(s) into the cannula after the cannula has been positioned and the guidewire removed. In preferred embodiments, placement of the guidewire is preceded by an aspirator tube, and fluids emerging from the tube are monitored by the operator to determine whether delicate tissue or structures adjacent to the ligament have been penetrated or compromised. In further preferred embodiments, an endoscope or other visualization device is inserted in the cannula to permit observation of the cutting operation.

A further novel feature is a unique cutting device suitable for insertion through the cannula. The cutting device includes a pair of elongated structural members, preferably joined by a linkage that permits longitudinal movement of one relative to the other. A cutting edge or blade is pivotally mounted to the distal end of one of the structural members, and the other structural member engages the blade in a manner causing the blade to pivot as one structural member is moved relative to the other. The blade can thus be moved from a retracted position to an extended or operative position, thereby permitting the operator to deploy and retract the blade from the proximal end of the device while the device is fully in place beneath and up against the ligament to be cut.

The invention offers a number of advantages to the operator. The composite device and its components, for example, are capable of being constructed with a small diameter, which reduces the level of trauma entailed in the procedure. Furthermore, the cutting blade is considerably easier to control in terms of its height as it protrudes from the cannula due to the remote deployment mechanism, and its position against the ligament, due to the pressure exerted by the inflatable member. Control of the cutting edge or blade helps the operator achieve a controlled cut while avoiding damage to the surrounding tissue, and the inflatable member helps maintain traction of the cannula in the cavity or passage beneath the ligament. The visualization provides further control.

The use and functions of these and other features and advantages of the invention will become more apparent from the description that follows and the attached drawings.

BRIEF DESCRIPTION OF THE DRAWINGS

FIG. 1 is a side view of a cannula in accordance with the present invention.

FIG. 2 is a side view of the cannula of FIG. 1, with the distal balloon inflated.

FIG. 3 is a cross section of the cannula of FIGS. 1 and 2, with the distal balloon inflated, taken along the plane indicated by the line 3—3 of FIG. 2.

FIG. 10 is a longitudinal cross section of a patient's hand undergoing a third step of the procedure, in which the cannula is being inserted in the carpal tunnel over the exchange wire.

FIG. 11 is a longitudinal cross section of a patient's hand undergoing a fourth step of the procedure, in which the distal balloon of the cannula has been inflated.

DETAILED DESCRIPTION OF THE INVENTION AND PREFERRED EMBODIMENTS

Figure 4:
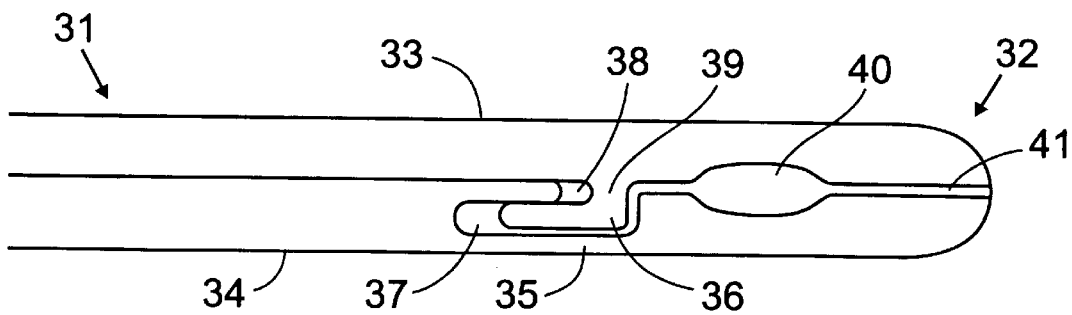
FIG. 4 is a top view of the distal end of a cutting device in accordance with the present invention.

While the invention is generic in nature and susceptible to a range and variety of embodiments, a better understanding will be attained by a detailed explanation of certain specific structures and their use, as represented by the drawings and described below.

An example of the cannula 11 that serves as a guide for the cutting device and any other operative components that are used in the carpal tunnel is shown in FIGS. 1, 2, and 3. The cannula is constructed from a length of tubing 12, that is preferably no more than 12 inches (30 cm) in length, more preferably from about 2 to about 12 inches (5 cm to 30 cm), and most preferably from about 3 to about 8 inches (7.6 cm to 20 cm). The tubing has a lateral opening 13 on one side (FIG. 3), which in use is the side facing the carpal ligament. This opening either extends the full length of the tubing or is restricted to a region adjacent to the distal end of the tubing. In the views shown in FIGS. 1 and 2, the distal end is the end at the right, and is the end that is inserted into the carpal tunnel. The end at the left is the proximal end, which remains outside the patient's body and is manipulated by the operator. This length of tubing can be constructed of any rigid material that is physiologically acceptable for percutaneous insertion into a bodily cavity. The term "physiologically acceptable" is used herein to denote a material that is inert to the physiological environment and capable of being sterilized for use in a surgical procedure. One presently preferred material is hypodermic tubing of 304 stainless steel with an internal diameter of 0.095 inch (0.24 cm), an external diameter of 0.110 inch (0.28 cm) and a length of about 5 inches (12.7 cm). These dimensions are not critical, however, and may vary. The opening 13 can be formed by removing one side of the tube by conventional methods such as grinding or electric discharge machining.

At the distal end of the tubing 12 is a blunt end cap 14, which eliminates sharp edges from exposure and provides a curved or rounded contour to minimize or eliminate any potential trauma or tissue damage upon insertion of the cannula into the patient. The cap 14 has a small central hole which permits passage of a guidewire 15 (the guidewire shown in FIG. 1). The cap material is likewise constructed of any rigid material that is physiologically acceptable for percutaneous insertion into a bodily cavity. One presently preferred material is a thermoplastic such as acrylonitrile-butadiene-styrene copolymer, with a length of about 0.125 inch (0.32 cm), the guidewire hole being about 0.020 inch (0.05 cm) in diameter. At the proximal end of the tubing 12 is a hollow knurled ring handle 16 permitting the operator to maintain a comfortable grip on the cannula. In a presently preferred construction, the ring 16 is of acrylonitrile-butadiene-styrene copolymer with an outer diameter of about 0.25 inch (0.64 cm), an inner diameter of about 0.110 inch (0.28 cm), and a length of about 0.25 inch (0.64 cm).

An inflatable member or balloon 21 is secured to the side of the tubing opposite the side where the opening 13 is located. The balloon is shown in deflated condition in FIG. 1 (where the balloon is only partially visible), and in inflated condition in FIGS. 2 and 3. The balloon 21 preferably occupies only a portion of the tubing length adjacent to the distal end of the tubing 12. The balloon 21 is fully enclosed except at its proximal end, where it opens into a supply tube 22 for inflation and deflation which extends along the remaining length of the cannula and beyond. The balloon 21 and the supply tube 22 are formed of physiologically acceptable materials, particularly any flexible material that can be formed into a thin-walled tube. One presently preferred material is polyethylene-terephthalate formed by heat and pressure into a tube of about 0.40 inch (1.0 cm) in diameter to form the balloon 21, with a wall thickness of about 0.002 inch (0.005 cm), and a length of about 4 inches (10.2 cm). Typical supply tube dimensions are an inner diameter of about 0.015 inch (0.038 cm), a wall thickness of about 0.003 inch (0.0076 cm), and a length of about 6 inches (15.2 cm). preferably, the supply tubing is of the same material as and continuous with the balloon material.

Upon deflation, the balloon material can either shrink or fold, in either case placing it in close proximity to the tubing 12 so that it will pass into or out of the incision and the carpal tunnel with relative ease. The degree of expansion upon inflation will be any amount that is sufficient to brace the balloon in the carpal tunnel beneath the carpal ligament. The balloon 21, and preferably the supply tube 22 as well, will be affixed to the tubing 12 by conventional means, including mechanical means such as bands or clips, and chemical means such as commercially available adhesives.

To hold the deflated balloon 21 tightly against the cannula tubing 12 during insertion of the cannula, the tubing 12 and balloon 21 are encased in a retaining or protective sheath 23 (shown in FIG. 1 only). The sheath is not bonded to either the tubing or the balloon but instead is removable to expose the balloon. The sheath can be removable by peeling away from the tubing and balloon, or by sliding off the tubing and balloon in the axial direction, or by both. In the view shown in FIG. 1, the sheath 23 is partially removed by having been drawn in the proximal direction.

The sheath 23 is preferably formed of a flexible, lubricious material, such as a tubular polyethylene extrusion. Removal of the sheath can be facilitated by constructing the sheath to contain a scored line or a line of relatively thin or otherwise weak material 24 running axially along the length of the sheath, to separate readily upon manual pressure. Preferably, the sheath contains two such lines on opposite sides, permitting the sheath to be easily split into two longitudinal halves as shown in FIG. 1, where the sheath is being pulled off and split simultaneously.

At the proximal end of the supply tube 22 is an additional balloon or bladder 25 that serves to absorb pressure increases imposed on the balloon 21 at the distal end of the cannula when the distal end balloon 21 encounters the restricting walls of the carpal tunnel. Upstream of the balloon is a shutoff valve 26 and a syringe 27. The proximal balloon 25 thus serves as a means of maintaining a substantially constant pressure in the inflation system when the shutoff valve 26 is closed. Like all other components of the cannula and the composite device in general, the construction and dimensions of the constant pressure balloon 25 can vary widely. A typical constant pressure balloon can be of latex with an internal diameter (uninflated) of about 0.06 inch (0.15 cm), an outer diameter of about 0.18 inch (0.46 cm), and a length of about 1 inch (2.54 cm). The shutoff valve 26 can be any valve capable of retaining fluid at the typical pressure encountered in the carpal tunnel. A presently preferred valve is a two-position valve with female and male parts joined by LUER-LOK type fittings on either side. Inflation and deflation of the distal balloon 21 are controlled by the syringe 27, which supplies inflation media to the balloon. A convenient syringe is a 10 cc polyethylene syringe, although other sizes and materials will serve equally well.

Figure 5:
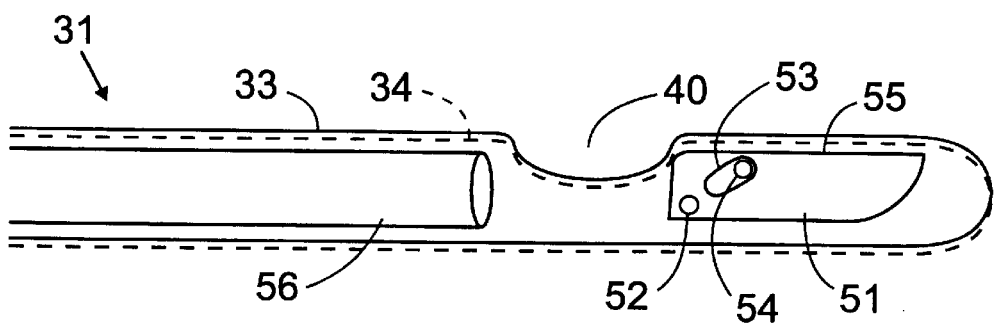
FIG. 5 is cross-sectional side view of the cutting device of FIG. 4.
Figure 6:
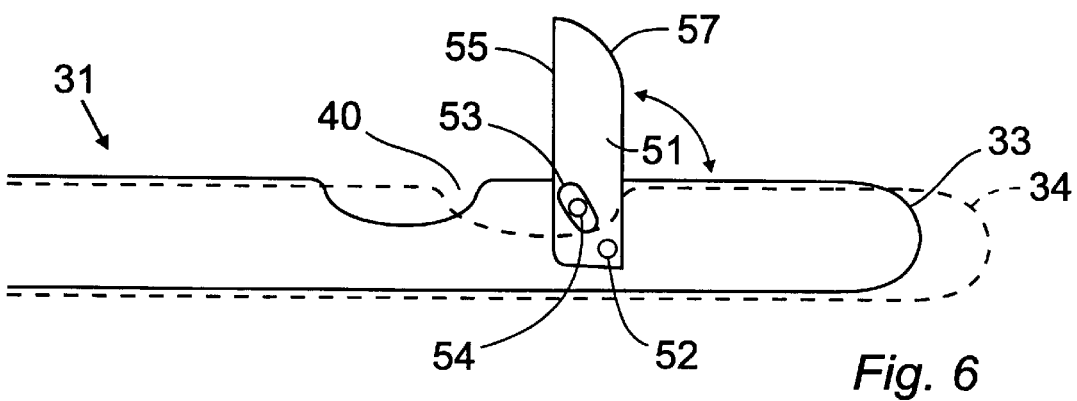
FIG. 6 is a further cross-sectional side view of the cutting device of FIG. 4, with the blade rotated into an operative position.

An example of the cutting device 31 is shown in FIGS. 4, 5, and 6. The exterior shape of this cutting device is that of a cylinder of diameter small enough to fit loosely inside, and slide axially and rotate within, the lumen of the cannula. The distal end 32 of the cylinder is rounded in shape to conform to the interior of the cannula end cap. FIG. 4 provides a top view of the cutting device, according to the orientation that the device will assume during use, and shows the two elongated structural members 33, 34 that form the exterior shape of the device. These two members are two longitudinal halves of the cylindrical tube, which is hollow, defining an internal lumen that is preferably of a substantially constant diameter along its entire length. The straight edges of the two tube halves abut along their lengths from the proximal end (not shown, but to the left of the FIG.) distally up to a linkage 35. The linkage joins the two halves while allowing them to slide back and forth a short distance relative to each other. The linkage consists of a hook 36 extending from one of the two halves and a slot 37 cut into the other, both elongated in the axial direction. The slot 37 is longer than the hook 36, and the slot entrance 38 is wider than the neck 39 of the hook, thereby permitting either one to be moved longitudinally relative to the other while the two remain engaged. Preferably, the cutting device contains a plurality of linkages of the type shown, spaced along the length of the device and on both top and bottom.

Distal to the linkage 35 (or to the most distally positioned linkage), the longitudinal edges of the two tube halves separate along the top of the cutting device, leaving a relatively wide opening 40 for the passage of light from an endoscope or other visualization component, and a narrower opening 41 from which the cutting blade, shown in FIGS. 5 and 6, will emerge.

The cutting device 31 is rotated 90° about its longitudinal axis in FIGS. 5 and 6 to provide a side view. The two halves are differentiated by showing the forward half 34 in dashed lines and the rear half 33 in solid lines. A blade 51 is mounted to the interior of the forward half 34, by a single pivot joint 52. The blade is flat and parallel to the planes of FIGS. 5 and 6, and the pivot joint 52 allows the blade to rotate in the same plane. An angled slot 53 in the blade receives a pin 54 that is mounted to the interior of the rear half 33 of the device.

FIG. 5 shows the device with both halves 33, 34 aligned, while FIG. 6 shows the configuration of the device with the rear half 33 moved in the proximal direction (i.e., to the left) relative to the forward half 34. The pin 54 has traveled within the slot 53 and drawn the blade up to rotate about the pivot joint 52 in the counterclockwise direction. The cutting edge 55 of the blade, formerly fully retained in the interior of the hollow cylinder that forms the cutting device, now protrudes through the opening 41 (FIG. 4) to divide the carpal ligament. Alternatively, the same result can be achieved by moving the forward half 33 in the distal direction (i.e., to the right).

The angle of the cutting edge 55 and the distance by which it protrudes from the hollow cylinder are governed by the amount of displacement of the two halves 33, 34 of the cylinder relative to each other. This permits the operator a high degree of control over the cutting operation. The operator can thus elect to cut the carpal ligament only partially to a selected depth, or to sever the ligament completely. In either case, cutting can be achieved by simply rotating the blade between the retracted position of FIG. 5 and the fully extended position of FIG. 6, or any degree of rotation in between, or by drawing the entire cutting device in the proximal direction, with the two halves fixed in position relative to each other, or by a combination of both movements. Cutting can also be performed in increments and at multiple locations on the carpal ligament, by effecting a first cut, then retracting the blade and moving the cutting device forward or back axially, rotating it about its axis, or both, then performing a second cut, followed by further orientations of the blade and further cuts if desired. While the cutting edge 55 is straight in the particular device shown in these FIGS., blades with curved cutting edges can also be used, either convex or concave, the blade being either planar or non-planar (cylindrical, for example). As a further variation, the distal edge 57 of the blade (when raised as shown in FIG. 6) can be the cutting edge, or both the proximal 55 and distal 57 edges. Cutting can then be achieved by the operator either pulling on the cutting device or pushing it.

The two halves 33, 34 of the cylindrical portion of the cutting device can be fabricated from any conventional material that is physiologically acceptable, and the length and diameter can vary widely. In a presently preferred example, the halves are made from commercially available hypodermic tubing of 304 stainless steel with an inner diameter of about 0.08 inch (0.20 cm), an outer diameter of about 0.09 inch (0.23 cm) and a length of about 5 inches (12.7 cm). The two halves can be cut from a single whole tube by conventional means, such as electric discharge machining. The blade can be surgical steel or a ceramic material capable of maintaining a durable and sharp cutting edge. A preferred material is photochemically etched surgical stainless steel. The dimensions may vary, a typical example being 0.08 inch (0.20 cm) in width, 0.40 inch (1.0 cm) in length, and 0.02 inch (0.05 cm) in thickness.

Due to the hollow tubular construction of the cutting device, an endoscope 56 (shown in FIG. 5) or other visualization device can be placed inside the cutting device from the proximal end and advanced in the distal direction to a location close to the wide opening 40 formed by the two halves of the cylinder. Any known device capable of transmitting an image of the surrounding area can be used, including commonly available endoscopes. One example of a suitable endoscope is "MINI-SITE," a 2-mm laparoscope with 0 ° direction available from United States Surgical Corporation, Norwalk, Conn., USA. The endoscope can be secured within the cutting device by O-rings contained within o-ring grooves to achieve a friction fit that will prevent axial and radial dislocation of the endoscope. The O-rings and o-ring grooves are preferably located at the proximal end of the cutting device. The distal end of the endoscope is preferably positioned such that the blade 51 is within the view of view of the endoscope at all times and at all orientations of the blade.

Figure 7:
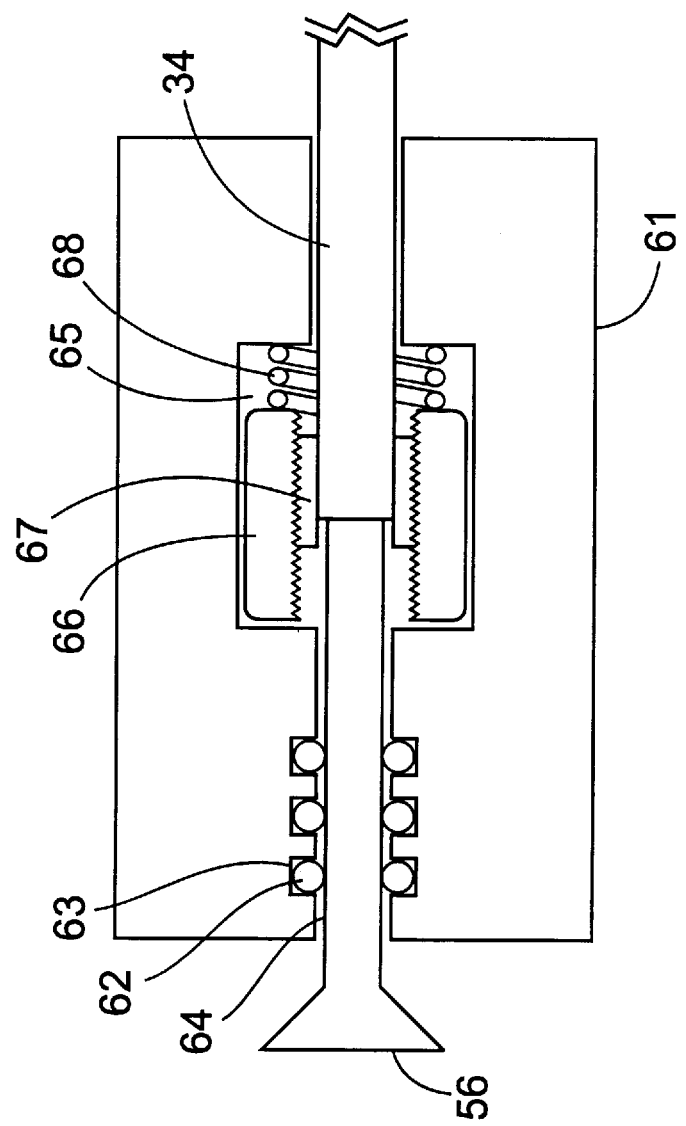
FIG. 7 is a longitudinal cross section of a handle at the proximal end of the cutting device of FIGS. 4, 5, and 6.

The proximal end of the cutting device 31 is shown in FIG. 7. This FIG. is a cross section of a handle 61 that is designed to be grasped by the operator, to secure the positions of the endoscope 56 and the two tubes halves 33, 34 of the cutting device (tube half 34 is the only one visible in FIG. 7), and to permit the operator to rotate the blade at the distal end of the cutting device by moving one tube half relative to the other from the proximal end in a controlled manner. The O-rings 62 referred to above, which secure the endoscope to the cutting device, are shown in FIG. 7. The O-rings are captured in grooves 63 cut in the inner wall of an axial passage 64, through which the endoscope 56 and cutting device tube halves 33, 34 pass.

The axial passage 64 opens into a central cavity 65 which accommodates an actuator knob 66. The central cavity 65 is open at both sides to permit operator access to the actuator knob 66, which rotates freely within the cavity about the longitudinal axis of the axial passage 64, while being captured within the cavity. The interior of the actuator knob 66 is threaded to mate with a threaded outer surface of a sleeve 67 affixed to the end of one of the two half tubes 33, 34 of the cutting device, thereby permitting closely controlled operator manipulation of the orientation of the blade at the distal end of the cutting device by simply rotating the actuator knob. A tensioned coil spring 68 or equivalent tensioning device inside the cavity 65 further secures the positions of the actuator knob and the tube halves. These components can be constructed from conventional materials, and their sizes, shapes and dimensions can vary. The handle 61 may for example be constructed of injection molded acrylonitrile-butadiene-styrene copolymer. Typical O-rings suitable for use are those with inner diameter of 1/16 inch (0.16 cm) and outer diameter of 3/16 inch (0.48 cm).

The components described above can be used in various procedures for the removal of swollen ligaments or the partial or complete division of ligaments to ease pressure or to otherwise repair a variety of conditions. Transecting of a carpal ligament is one example of such a procedure; and the removal of the patellar ligament is another. The components can be used alone or in conjunction with other components. One preferred method of using these components is described below and shown in FIGS. 8 through 12. This particular method is illustrated in the context of carpal tunnel syndrome and involves entering the carpal tunnel through an incision in the wrist of the patient, and advancing the cannula and cutting device assembly in the direction of the fingers. The same procedure can be performed through an incision in the palm of the patient, with the cannula and cutting device assembly being advanced in the direction of the wrist. In general, the incision will be located laterally relative to the target ligament, and the direction of advancement of the cannula and cutting device assembly will be transverse to the ligament.

Figure 8:
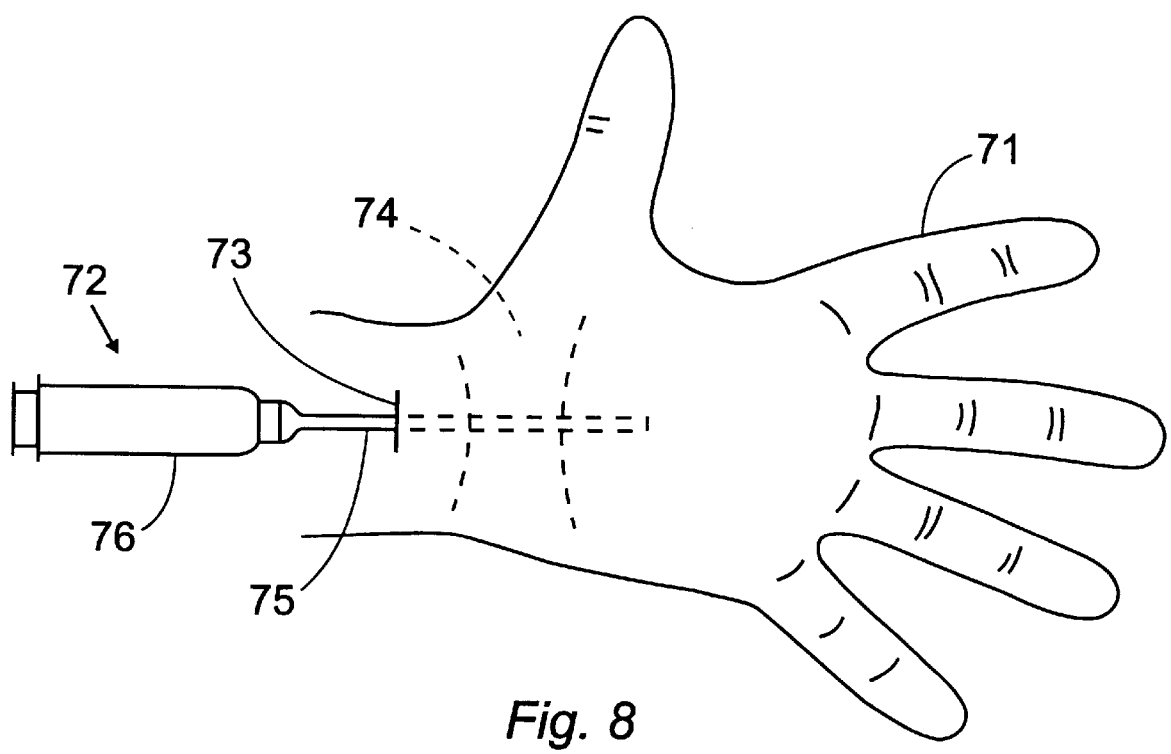
FIG. 8 is a top view of a patient's hand undergoing a first step of a procedure in accordance with this invention, in which a blunt needle is being inserted beneath the carpal ligament, with a syringe barrel secured to the needle.

FIG. 8 shows the patient's hand 71 with the palm side up (facing the viewer). This procedure is begun by inserting a syringe 72 and needle 75 through an incision 73 in the patient's wrist, and advancing the syringe needle into the carpal tunnel and beneath the carpal ligament 74, in the direction of the patient's fingers. The syringe 72 has a blunt-tipped needle 75, which can be fabricated from any moldable or malleable tubular material. One example is hypodermic tubing of 304 stainless steel with inner diameter of about 0.020 inch (0.051 cm), outer diameter of 0.030 inch (0.076 cm), length of about 6 inches (15.2 cm), and a partially closed or rounded end. The needle can be secured to the syringe barrel with a conventional fitting, such as a LUER-LOK type fitting.

As the blunt-tipped needle 75 is advanced beneath the carpal ligament, fluid from the carpal tunnel is aspirated by the syringe and visually monitored by the operator through the syringe barrel 76. The operator can thus determine when a delicate structure within or adjacent to the carpal tunnel has been violated, and can correct this by retracting the needle a short distance without causing significant damage to the structure. The position of blunt-tipped needle 75 is monitored by palpating the patient's palmar surface.

Figure 9:
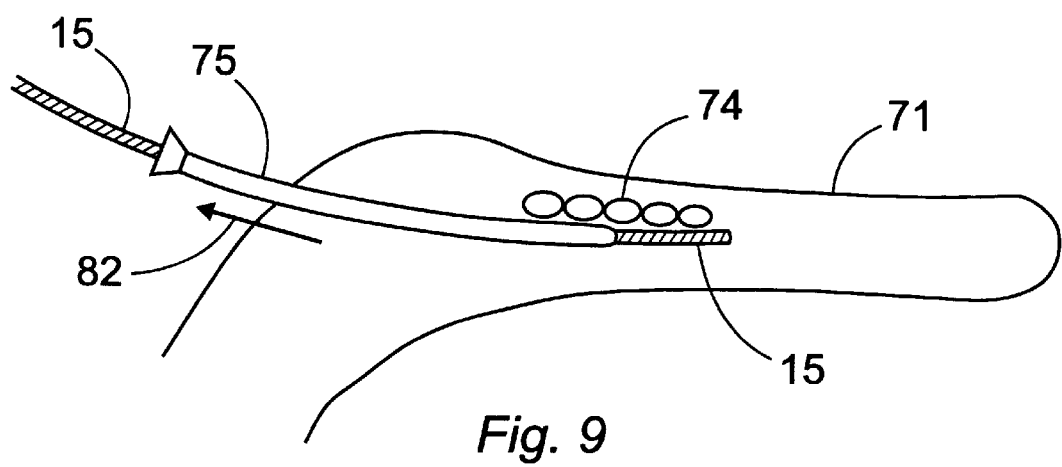
FIG. 9 is a longitudinal cross section of a patient's hand undergoing a second step of the procedure, in which an exchange wire has been introduced into the carpal tunnel through the blunt needle, and the blunt needle is being withdrawn.

Once the blunt-tipped needle 75 is in position, the syringe barrel 76 is removed, and a guidewire or exchange wire 15 is inserted through the needle and out the distal end of the needle, as shown in FIG. 9. The exchange wire can be any thin elongated member that fits easily within the syringe needle, and is flexible enough to follow the needle and the carpal tunnel without puncturing any tissues within the patient's hand, yet has sufficient column strength to allow it to be advanced from the proximal end without bending or forming kinks. A convenient material of construction is a unifilar, round coil wire of 304 stainless steel with an external diameter of about 0.018 inch (0.046 cm) and a length of about 12 inches (30.5 cm).

Once the exchange wire 15 is in place, the syringe needle 75 is withdrawn back through the incision (in the direction of the arrow 82 and removed from the proximal end of the exchange wire, leaving the exchange wire alone in the carpal tunnel. The cannula 11, without the cutting device, is then advanced as shown in FIG. 10 in the direction of the arrow 83, over the exchange wire 15, through the incision and under the carpal ligament. The exchange wire 15 is then removed from the cannula lumen, and the sheath 23 is removed from the exterior of the cannula. The balloon 21 is then inflated, as shown in FIG. 11, securing the cannula in place and urging the cannula against the underside of the carpal ligament 74. The shutoff valve 26 (FIGS. 1 and 2) is then closed and the syringe 27 removed to clear the operational field.

Figure 12:
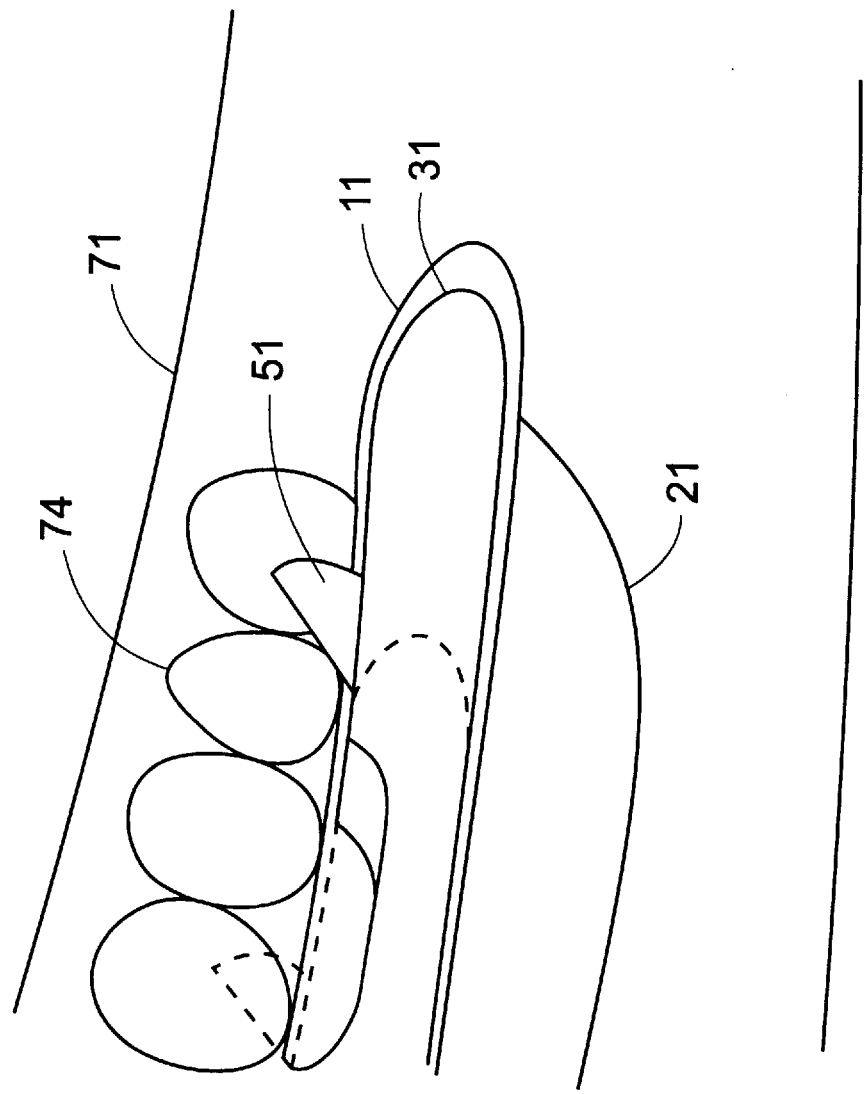
FIG. 12 is an enlarged longitudinal cross section of a patient's hand undergoing a fifth step of the procedure, in which the carpal ligament is being cut by the cutting device.

The cutting device assembly is then prepared outside the patient by inserting the endoscope into the device and adjusting the blade to hold it in the retracted position as shown in FIG. 5. The assembly is then inserted through the cannula, into the position shown in the enlarged view of FIG. 12. The operator uses the endoscope to identify the tissues to be divided, positions the distal end of the cutting device 31, and raises the blade 51 by rotation of the actuator knob at the proximal end. With the blade raised, the operator slowly draws the cutting device across the tissue, with the inflated balloon 21 stabilizing the blade against the tissue 74 as the blade spreads the carpal ligament. Depending on the condition of the patient and the needs of the procedure, the operator can complete the operation with a single pass of the blade, or with multiple passes between which the balloon can be deflated, the blade retracted, or both, and the cannula and cutting device either moved axially, rotated, or both, before reinflating the balloon and returning the blade to a raised position. The terms "spreading" and "transecting" are used herein to indicate any type of cut in the carpal ligament that will relieve pressure in the carpal tunnel. This can include a partial cut in the ligament, extending less than the full thickness of the ligament, or a full cut, severing the ligament entirely. Following the cut, the blade can be retracted and the cutting device moved in the axial direction where the blade is raised once again for a second or subsequent cuts. This is represented in FIG. 12 by the dashed line. The movement between cuts can also be radial, resulting in cuts at different transverse locations on the same ligament.

Upon completion of the procedure, the blade 51 is fully retracted into the cutting device 31, and the cutting device, endoscope and cannula are removed. The incision is then sutured, closed with a butterfly-type bandage, or otherwise treated in accordance with conventional procedures. The procedure is thus performed without surgical opening of the hand or any incisions other than the single incision in the patient's wrist (or palm).

Figure 13:
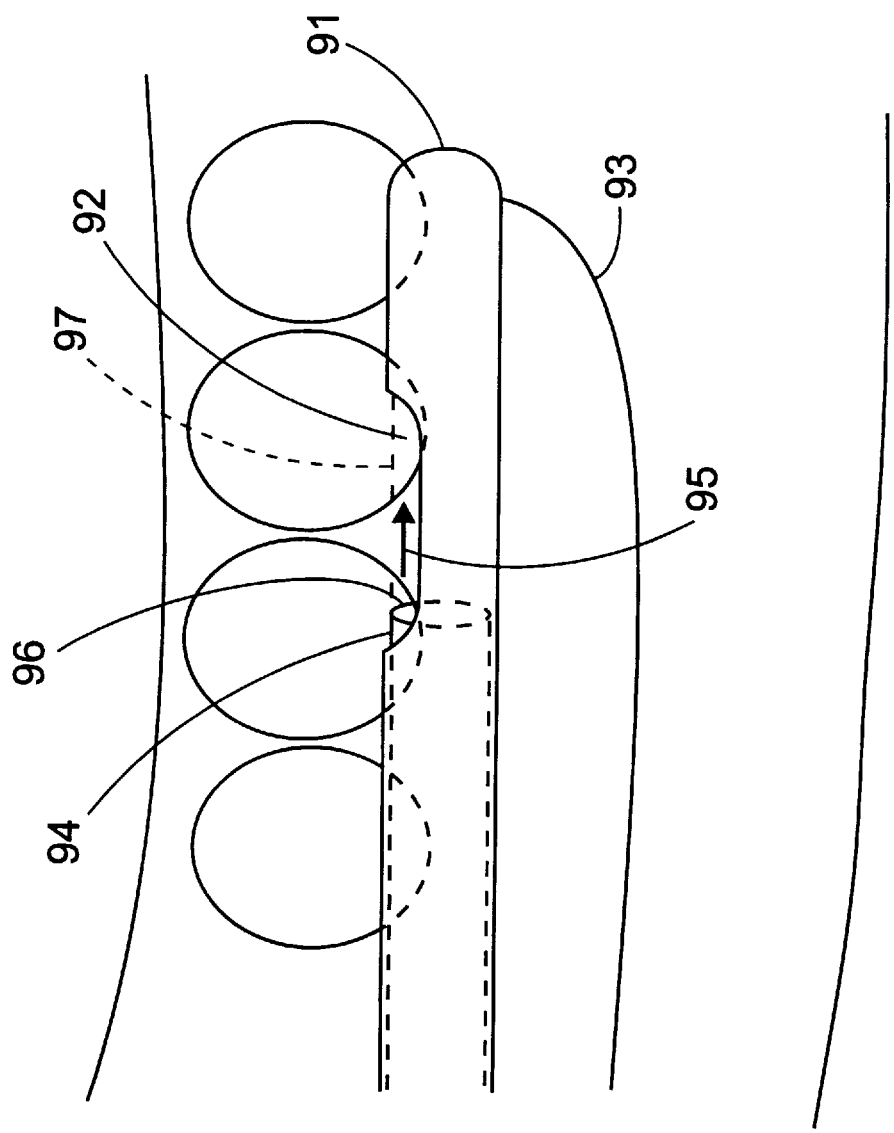
FIG. 13 is a side view of a second cannula and cutting device within the scope of this invention, in an enlarged cross section of a patient's hand.

An alternative cannula and cutting device are shown in FIG. 13. This cannula 91 has an opening 92 on its upper side, but the opening 92 extends only a short distance along the cannula length. A balloon 93 similar to that on the cannula in the preceding drawings is affixed to the bottom side of the cannula. The cutting device 94 is a hollow cylinder that is received within the lumen of the cannula 91, and is movable in the axial direction within the cannula, as indicated by the arrow 95. The leading edge at the distal end of the cutting device is a sharpened cutting edge 96. When the balloon 93 is inflated, ligament or other tissue facing the opening 92 in the cannula protrudes into the opening. Advancement of the cutting device 94 causes the cutting edge 96 to sever the portion of the ligament or tissue at the dashed line 97. Multiple passes of the cutting edge can be made for further clearance. The loosened material is retained in the cutting device and cannula and removed when these components are withdrawn. The cutting device 94 can also assume other configurations while operating in the same manner. For example, the cutting edge 96 can be angled relative to the axis of the cannula and cutting device, or the cutting edge can be the sharpened edge of a lateral opening in the cutting device. Still further configurations will be readily apparent to those skilled in the art.

The cannula and cutting device of FIG. 13 can be inserted in the patient in the same manner as the cannula and cutting device of the preceding drawings, i.e., by first inserting a blunt-tipped needle, then an exchange wire, removing the blunt-tipped needle leaving the exchange wire in place, inserting the cannula over the exchange wire, removing the exchange wire, and then inserting the cutting device. The retracted position of the cutting device of FIG. 13 is one in which the cutting edge 96 is clear of the opening 92 (either proximally or distally) and thereby not exposed to the ligament, and the operating position is one in which the cutting edge 96 is underneath the opening and in direct contact with ligament tissue protruding into the opening.

The foregoing is offered primarily for purposes of illustration, it will be readily apparent to those skilled in the surgical and medical device arts that the materials, dimensions, sequence of use, and various other parameters of the structures and methods disclosed herein can be further modified or substituted without departing from the spirit and scope of the invention.

We claim:

1. A device for transecting a ligament, comprising:
    a cannula not exceeding twelve inches in length and having proximal and distal ends, each with openings, said cannula defining a lumen and having a lateral opening on one side thereof adjacent to said distal end;
    an inflatable member affixed to an external surface of said cannula adjacent to said distal end and opposite said lateral opening, and means for supplying inflation fluid to said inflatable member from said proximal end of said cannula; and
    a cutting member on an elongate support equal in length to or longer than said cannula;
    said opening at said proximal end being large enough to receive said cutting member and said lumen being large enough to permit passage of said cutting member from said proximal end opening to said lateral opening.

2. A device in accordance with claim 1, further comprising:
    a protective sheath encasing said cannula and said inflatable member, said protective sheath capable of being manually drawn off said device from said proximal end of said cannula.

3. A device in accordance with claim 1, in which said lumen has a substantially constant internal diameter from said proximal end of said cannula to said lateral opening.

4. A device in accordance with claim 1, in which said cannula is from about two inches to about twelve inches in length.

5. A device in accordance with claim 1, in which said cannula is from about three inches to about eight inches in length.

6. A device in accordance with claim 1, in which said means for supplying inflation fluid to said inflatable member is a supply tube extending along the exterior of said cannula from said inflatable member to said proximal end.

7. A device in accordance with claim 1, in which said opening at said distal end of said cannula is substantially smaller than said opening at said proximal end, and said distal end of said cannula is narrowed in a rounded configuration.

8. A cutting device for remote actuation through a cannula, said cutting device comprising:
   first and second elongate members, each having proximal and distal ends and each being longitudinally moveable relative to the other;
   a blade pivotally mounted to said first elongate member at said distal end thereof, and
   means on said second elongate member for engaging said blade and for causing said blade to pivot when one of said elongate members is moved longitudinally relative to the other;
   wherein said blade has a linear cutting edge, and said blade is pivotally mounted to said first elongate member to pivot between a retracted position in which said linear cutting edge is substantially parallel to said first elongate member and an exposed position in which said linear cutting edge is transverse to said first elongate member.

9. A cutting device in accordance with claim 8, in which said first and second elongate members together comprise two longitudinal sections of a tubular member having a lumen.

10. A cutting device in accordance with claim 9, in which said blade has a cutting edge, and said blade is pivotally mounted to said first elongate member to pivot between a retracted position in which said entire cutting edge is retained within said lumen and an exposed position in which at least a portion of said cutting edge is outside said lumen.

11. A cutting device in accordance with claim 9, further comprising visualization means disposed in said lumen and in which said tubular member has a lateral opening through which regions external to said cutting device can be observed through said visualization means.

12. A cutting device in accordance with claim 11, in which said visualization means is an endoscope.

13. A cutting device in accordance with claim 8, in which said first and second elongate members are joined by a movable linkage permitting a range of motion of from about 1 mm to about 5 mm.

14. A cutting device in accordance with claim 8, further comprising means at said proximal ends of said first and second elongate members for fixing the positions of said first and second elongate members relative to each other over a continuous range.

15. A device for transecting a ligament, comprising:
   a cannula having proximal and distal ends, with an opening at said proximal end, said cannula defining a lumen and having a lateral opening on one side thereof adjacent to said distal end;
   an inflatable member affixed to an external surface of said cannula adjacent to said distal end and opposite said lateral opening, and means for supplying inflation fluid to said inflatable member from said proximal end of said cannula; and
   a cutting member comprising (a) first and second elongate members, each having proximal and distal ends and each being longitudinally movable relative to the other;
   (b) a blade pivotally mounted to said first elongate member at said distal end thereof; and (c) means on said second elongate member for engaging said blade and for causing, by the longitudinal movement of one of said elongate members relative to the other, said blade to pivot between a retracted position in which said blade is fully retained inside said cannula lumen and an exposed position in which said blade protrudes through said lateral opening of said cannula;
   said opening at said proximal end of said cannula being large enough to receive said cutting member and said cannula lumen being large enough to permit passage of said cutting member from said proximal end opening to said lateral opening.

16. A device in accordance with claim 15, in which said cannula lumen has a substantially constant internal diameter from said proximal end of said cannula to said lateral opening of said cannula.

17. A device in accordance with claim 15, in which said cannula is from about two inches to about twelve inches in length, and said means for supplying inflation fluid to said inflatable member is a supply tube extending along the exterior of said cannula from said inflatable member to said proximal end.

18. A device in accordance with claim 15, in which said cannula lumen has a substantially constant internal diameter from said proximal end of said cannula to said lateral opening of said cannula, and said first and second elongate members of said cutting member together comprise two longitudinal sections of a tubular member defining a cutting member lumen, said tubular member sized to be received within said cannula lumen and to slide longitudinally therethrough.

19. A device in accordance with claim 18, further comprising visualization means disposed in said cutting member lumen and in which said cutting member lumen has a lateral opening through which regions external to said cutting device can be observed through said visualization means.

20. A method for transecting a ligament in a patient, said method comprising:
   (a) inserting a cannula through an incision in said patient located laterally relative to said ligament, said cannula having a lateral opening on one side thereof and an inflatable member affixed to an external surface thereof on a side opposite that of said lateral opening, and advancing said cannula to a position adjacent and transverse to said ligament, whereby said lateral opening resides adjacent to said ligament;
   (b) inserting a cutting member into said cannula, said cutting member having proximal and distal ends and containing a cutting edge at said distal end and movable from said proximal end between a retracted position and an operating position, and advancing said cutting member through said cannula to a position whereby said cutting edge is adjacent to said lateral opening;
   (c) inflating said inflatable member to urge said lateral opening against said ligament;
   (d) moving said cutting edge to said operating position whereby said cutting edge engages said ligament; and
   (e) traversing said ligament with said cutting edge.

21. A method in accordance with claim 20, further comprising, prior to (a):
   (i) inserting a tubular member through said incision and advancing said tubular member adjacent to said ligament to traverse said ligament;
   (ii) inserting an exchange wire through said tubular member while said tubular member traverses said ligament; and (iii) withdrawing said tubular member over said exchange wire without withdrawing said exchange wire;

and in which (a) comprises advancing said cannula over said exchange wire, then removing said exchange wire without removing said cannula.

22. A method in accordance with claim 21, further comprising aspirating fluid through said tubular member during (i), and observing fluid thus aspirated as an indication of the position of a distal end of said tubular member.

23. A method in accordance with claim 22, in which said cutting member is a cylinder and said cutting edge is a distal open end of said cylinder, and (d) comprises advancing said cylinder axially.

24. A method in accordance with claim 20, in which said cutting edge is an edge of a flat blade, and (d) comprises raising said blade through said lateral opening in said cannula.

25. A method in accordance with claim 20, further comprising inserting visualization means into said cannula prior to (d), and performing (d) and (e) while visualizing motion of said cutting edge.

26. A method in accordance with claim 20, further comprising inserting visualization means into said cannula simultaneous with (b), and performing (d) and (e) while visualizing motion of said cutting edge.

27. A method in accordance with claim 20, in which said cutting member comprises a tubular shaft with said cutting edge at said distal end thereof, said method further comprising inserting visualization means through said tubular shaft of said cutting member, and performing (d) and (e) while visualizing motion of said cutting edge.

28. A method in accordance with claim 27, in which said tubular shaft of said cutting member is longitudinally divided into first and second segments, each forming approximately one half of said tubular shaft, said cutting edge is a flat blade pivotally mounted to said first segment, and said second segment engaging said blade in a manner causing said blade to pivot when one of said segments is moved longitudinally relative to the other, and (d) comprises longitudinally moving one of said segments relative to the other.

29. A method in accordance with claim 20, in which said cannula and cutting member have longitudinal axes and (e) comprises drawing said cutting edge across said ligament at a first transverse location thereon, said method further comprising, subsequent to (e):

(f) moving said cutting edge to said retracted position and rotating said cannula and cutting member about their longitudinal axes to align said cutting edge with a second transverse location across said ligament; and (g) moving said cutting edge to said operating position and drawing said cutting edge across said ligament at said second transverse location.

30. A method in accordance with claim 20, in which (a) comprises advancing said cannula to place said lateral opening at a first axial position beneath said ligament, and (e) comprises drawing said cutting edge across a first portion of a transverse plane of said ligament, said method further comprising, subsequent to (e):

(f) moving said cutting edge to said retracted position and moving said cannula axially to a second axial position beneath said ligament, said second axial position being aligned with a second portion of said transverse plane; and (g) moving said cutting edge to said operating position and drawing said cutting edge across said second portion.

31. A method in accordance with claim 20, in which said ligament is carpal ligament, said incision is in the wrist of said patient, and (a) comprises advancing said cannula through said carpal tunnel.

* * * * *